(12) United States Patent
Erlander et al.

(10) Patent No.: US 9,670,553 B2
(45) Date of Patent: Jun. 6, 2017

(54) DETERMINING TUMOR ORIGIN

(71) Applicant: bioTheranostics, Inc., San Diego, CA (US)

(72) Inventors: Mark Erlander, Carlsbad, CA (US); Xiao-Jun Ma, San Diego, CA (US)

(73) Assignee: bioTheranostics, Inc., San Diego, CA (US)

( * ) Notice: Subject to any disclaimer, the term of this patent is extended or adjusted under 35 U.S.C. 154(b) by 0 days.

(21) Appl. No.: 14/810,323

(22) Filed: Jul. 27, 2015

(65) Prior Publication Data
US 2015/0329921 A1    Nov. 19, 2015

Related U.S. Application Data

(63) Continuation of application No. 13/083,552, filed on Apr. 9, 2011, now abandoned, and a continuation-in-part of application No. 11/145,307, filed on Jun. 3, 2005, application No. 14/810,323, which is a continuation-in-part of application No. 11/422,056, filed on Jun. 2, 2006.

(60) Provisional application No. 60/577,084, filed on Jun. 4, 2004, provisional application No. 60/687,174, filed on Jun. 3, 2005.

(51) Int. Cl.
*C12Q 1/68* (2006.01)

(52) U.S. Cl.
CPC ......... *C12Q 1/6888* (2013.01); *C12Q 1/6886* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 7,514,209 B2 | 4/2009 | Dai et al. | |
| 2002/0110820 A1 | 8/2002 | Ramaswamy et al. | |
| 2003/0017481 A1 | 1/2003 | Golub et al. | |
| 2003/0138793 A1* | 7/2003 | Su | C12Q 1/6886 435/6.14 |
| 2003/0148295 A1 | 8/2003 | Wan et al. | |
| 2003/0219767 A1 | 11/2003 | Ayers et al. | |
| 2003/0224374 A1 | 12/2003 | Dai et al. | |
| 2003/0225526 A1 | 12/2003 | Golub et al. | |
| 2003/0225528 A1 | 12/2003 | Baker et al. | |
| 2004/0002067 A1 | 1/2004 | Erlander et al. | |
| 2004/0098367 A1 | 5/2004 | Tamayo et al. | |
| 2004/0253606 A1 | 12/2004 | Aziz et al. | |
| 2005/0003341 A1 | 1/2005 | Polansky | |
| 2005/0208500 A1 | 9/2005 | Erlander et al. | |
| 2005/0260572 A1 | 11/2005 | Kato et al. | |
| 2005/0272061 A1* | 12/2005 | Petroziello | C12Q 1/6886 435/6.14 |
| 2006/0094035 A1 | 5/2006 | Erlander et al. | |
| 2006/0265138 A1* | 11/2006 | Bowtell | C12Q 1/6886 702/20 |
| 2006/0292572 A1 | 12/2006 | Stuart et al. | |
| 2007/0020655 A1 | 1/2007 | Erlander et al. | |
| 2009/0157326 A1 | 6/2009 | Dai et al. | |
| 2010/0178653 A1 | 7/2010 | Aharonov et al. | |
| 2010/0273172 A1 | 10/2010 | Rosenfeld et al. | |
| 2010/0323903 A1 | 12/2010 | Rosenwald et al. | |
| 2011/0077168 A1 | 3/2011 | Rosenfeld et al. | |
| 2011/0097756 A1 | 4/2011 | Hagmann et al. | |

FOREIGN PATENT DOCUMENTS

| | | | |
|---|---|---|---|
| WO | WO 01/94629 A2 | 12/2001 | |
| WO | WO 02/103320 A2 | 12/2002 | |
| WO | WO 03/041562 A2 | 5/2003 | |
| WO | WO 2005/059109 A2 | 6/2005 | |
| WO | WO 2006080597 A1 * | 8/2006 | ........... C12Q 1/6886 |
| WO | WO 2007/137366 A1 | 12/2007 | |
| WO | WO 2010/108638 A9 | 9/2010 | |

OTHER PUBLICATIONS

Iwao et al. (Molecular classification of primary breast tumors possessing distinct prognostic properties, Hum Mol Genet. Jan. 15, 2002;11(2):199-206).*
Buckhaults et al. (Identifying tumor origin using a gene expression-based classification map, Cancer Res. Jul. 15, 2003;63(14):4144-9).*
Dennis et al. (Identification from Public Data of Molecular Markers of Adenocarcinoma. Characteristic of the Site of Origin, Cancer Research, vol. 62, No. 21, p. 5999-6005, Nov. 1, 2002).*
Tothill et al. (An expression-based site of origin diagnostic method designed for clinical application to cancer of unknown origin, Cancer Res. May 15, 2005;65(10):4031-40).*
Ramaswamy et al. (Multiclass cancer diagnosis using tumor gene expression signatures, Proc Natl Acad Sci U S A Dec. 18, 2001;98(26):15149-54. Epub Dec. 11, 2001).*
Golub et al. (Molecular classification of cancer: class discovery and class prediction by gene expression monitoring, Science. Oct. 15, 1999;286(5439):531-7).*
Su et al. (Molecular classification of human carcinomas by use of gene expression signatures, Cancer Res. Oct. 15, 2001;61(20):7388-93).*
Shedden et al. (Accurate molecular classification of human cancers based on gene expression using a simple classifier with a pathological tree-based framework, Am J Pathol. Nov. 2003;163(5):1985-95).*
Giordano et al. (Organ-specific molecular classification of primary lung, colon, and ovarian adenocarcinomas using gene expression profiles, Am J Pathol. Oct. 2001;159(4):1231-8).*
Ma et al. (Molecular classification of human cancers using a 92-gene real-time quantitative polymerase chain reaction assay, Arch Pathol Lab Med. Apr. 2006;130(4):465-73).*
López-Encuentra et al. (Comparison between clinical and pathologic staging in 2,994 cases of lung cancer, Ann Thorac Surg. Mar. 2005;79(3):974-9; discussion 979).*
CancerConnect.com (Pathology Tests, attached, available at http://news.cancerconnect.com/testingcenter/ Pathologytests, accessed Aug. 16, 2016).*
Erlander et al. (Performance and clinical evaluation of the 92-gene real-time PCR assay for tumor classification, J Mol Diagn. Sep. 2011;13(5):493-503. doi: 10.1016/j.jmoldx.2011.04.004. Epub Jun. 25, 2011).*
Kerr et al. (Multisite validation study to determine performance characteristics of a 92-gene molecular cancer classifier, Clin Cancer Res. Jul. 15, 2012;18(14):3952-60. doi: 10.1158/1078-0432.CCR-12-0920. Epub May 30, 2012).*

(Continued)

*Primary Examiner* — Aaron Priest
(74) *Attorney, Agent, or Firm* — Jones Day (57) ABSTRACT

The disclosure provides methods for the use of gene expression measurements to classify or identify among 54 cancer types in samples obtained from a subject in a clinical setting, such as in cases of formalin fixed, paraffin embedded (FFPE) samples.

15 Claims, 2 Drawing Sheets

(56) References Cited

OTHER PUBLICATIONS

Brachtel et al. (Molecular classification of cancer with the 92-gene assay in cytology and limited tissue samples, Oncotarget. May 10, 2016;7(19):27220-31. doi: 10.18632/oncotarget.8449).*
"Affimetrix GeneChip Human Genome U133 Array Set HG-U133A", GEO, abstract, XP002254749 (2002).
"Affymetrix Genechip bHuman Genome U133 plus 2.0 Array", GEO, abstract, XP002343693 (2003).
Barden et al., "Classification of follicular thyroid tumors by molecular signature: results of gene profiling", Clin Cancer Res., 9(5):1792-1800 (2003).
Bhattacharjee et al., "Classification of human lung carcinomas by mRNA expression profiling reveals distinct adenocarcinoma subclasses", Proc Natl Acad Sci USA, 98(24):13790-13795 (2001).
Bloom et al., "Multi-platform, multi-site, microarray-based human tumor classification", Am J Pathol., 164(1):9-16 (2004).
Bridgewater, et al., "Gene expression profiling may improve diagnosis in patients with carcinoma of unknown primary", Br J Cancer, 98(8):1425-1430 (2008).
Cole et al., "The genetics of cancer—a 3D model", Nat Genet., 21(1 Suppl):38-41 (1999).
Dash et al., "Distance Based Feature Selection for Clustering Microarray Data, in Database Systems for Advanced Applications", Eds. Tsuji, Jin, Higuchi, pp. 512-519 (2008).
Dennis et al., "Identification from public data of molecular markers of adenocarcinoma characteristic of the site of origin", Cancer Res., 62(21):5999-6005 (2002).
Dirisi et al., "Use of a cDNA microarray to analyse gene expression patterns in human cancer", Nat Genet., 14(4):457-460 (1996).
Epstein et al., "Microarray technology—enhanced versatility, persistent challenge", Curr Opin Biotechnol., 11(1):36-41 (2000).
Feng et al., "Molecular biomarkers for cancer detection in blood and bodily fluids", Crit Rev Clin Lab Sci., 43(5-6):497-560 (2006).
Glinsky et al., "Classification of human breast cancer using gene expression profiling as a component of the survival predictor algorithm", Clin Cancer Res., 10(7):2272-2283 (2004).
International Search Report and Written Opinion for PCT/US2015/019736 (17 pages).
Khan et al., "Classification and diagnostic prediction of cancers using gene expression profiling and artificial neural networks", Nat Med., 7(6):673-679 (2001).
Lockhart et al., "Genomics, gene expression and DNA arrays", Nature, 405(6788):827-836 (2000).
Ma et al., "Gene expression signatures associated with clinical outcome in breast cancer via laser capture microdissection", Breast Cancer Research and Treatment, 82(Suppl 1):S15.
Martin et al , "Linking gene expression patterns to therapeutic groups in breast cancer", Cancer Res., 60(8):2232-2238 (2000).
Nielsen et al., "Tissue microarray validation of epidermal growth factor receptor and SALL2 in synovial sarcoma with comparison to tumors of similar histology", Am J Pathol., 163(4):1449-1456 (2003).
Noonan et al., "Characterization of the homeodomain gene EMX2: sequence conservation, expression analysis, and a search for mutations in endometrial cancers", Genomics, 76(1-3):37-44 (2001).
Okada et al., "Analysis of gene-expression profiles in testicular seminomas using a genome-wide cDNA microarray", Int J Oncol., 23(6):1615-1635 (2003).
Osoegawa et al., "A bacterial artificial chromosome library for sequencing the complete human genome", Genome Res., 11(3):483-496 (2001).
Perou et al., "Distinctive gene expression patterns in human mammary epithelial cells and breast cancers", Proc Natl Acad Sci USA, 96(16):9212-9217 (1999).
Ramaswamy et al., "A molecular signature of metastasis in primary solid tumors", Nat Genet., 33(1):49-54 (2003).
Schena et al., "Quantitative monitoring of gene expression patterns with a complementary DNA microarray", Science, 270(5235):467-470 (1995).
Sgroi et al., "In vivo gene expression profile analysis of human breast cancer progression", Cancer Res., 59(22):5656-5661 (1999).
Sgroi et al., "In vivo gene expression profiling of human breast cancer", Laboratory Investigation, United States and Canadian Academy of Pathology, 82(1):51A.
Srinivas et al., "Trends in biomarker research for cancer detection", Lancet Oncol., 2(11):698-704 (2001).
Takahashi et al., "Gene expression profiling of clear cell renal cell carcinoma: gene identification and prognostic classification", Proc Natl Acad Sci USA, 98(17):9754-9759 (2001).
Tamayo et al., "Interpreting patterns of gene expression with self-organizing maps: methods and application to hematopoietic differentiation", Proc Natl Acad Sci USA, 96(6):2907-2912 (1999).
Van't Veer et al., "Gene expression profiling predicts clinical outcome of breast cancer", Nature, 415(6871):530-536 (2002).
Welford et al., "Detection of differentially expressed genes in primary tumor tissues using representational differences analysis coupled to microarray hybridization", Nucleic Acids Res., 26(12):3059-3065 (1998).
Winston, "Small Cell Lung Cancer", Medscape, accessed Feb. 17, 2015 http://emedicine.medscape.com/article/280104-overview.
Yeung et al., "Multiclass classification of microarray data with repeated measurements: application to cancer", Genome Biol., 4(12):R83 (2003).

* cited by examiner

DETERMINING TUMOR ORIGIN

CROSS-REFERENCE TO RELATED APPLICATIONS

This application is a continuation of prior application Ser. No. 13/083,552, filed Apr. 9, 2011. This application is also a continuation-in-part of prior application Ser. No. 11/145,307, filed Jun. 3, 2005, which claims the benefit of U.S. Provisional Application No. 60/577,084, filed Jun. 4, 2004. This application is also a continuation-in-part of prior application Ser. No. 11/422,056, filed Jun. 2, 2006, which claims the benefit of U.S. Provisional Application No. 60/60/687,174, filed Jun. 3, 2005.

FIELD OF THE DISCLOSURE

This disclosure relates to the use of gene expression to classify human tumors. The classification is performed by use of gene expression profiles, or patterns, of 50 or more, or optionally 5 or more, expressed sequences, where the sequences are expressed in more than one tumor type. The disclosure thus includes use of gene expression levels that overlap in more than one tumor type or tumors that arise from certain tissues. The disclosure also provides for the use of 50 or more, or optionally 5 or more, specific gene sequences, the expression of which are present in more than one tissue source of a tumor and so tumor or cancer type. The gene expression profiles, whether embodied in nucleic acid expression, protein expression, or other expression formats, may be used to determine a cell containing sample as containing tumor cells of a tissue type or from a tissue origin to permit a more accurate identification of the cancer and thus treatment thereof as well as the prognosis of the subject from whom the sample was obtained.

BRIEF SUMMARY OF THE DISCLOSURE

This disclosure relates to the use of gene expression measurements to classify or identify cancers and/or tumors in cell containing samples obtained from a subject in a clinical setting, such as in cases of formalin fixed, paraffin embedded (FFPE) samples as well as fresh samples, that have undergone none to little or minimal treatment (such as simply storage at a reduced, non-freezing, temperature), and frozen samples. The disclosure thus provides the ability to classify a sample under real-world conditions faced by hospital and other laboratories which conduct testing on clinical FFPE samples. The samples may be of a primary tumor sample or of a tumor that has resulted from a metastasis of another tumor. Alternatively, the sample may be a cytological sample, such as, but not limited to, cells in a blood sample. The disclosure may also be viewed as molecular profiling of an unknown cancer or tumor by predicting tissue of origin for the cancer or tumor.

In some cases of a tumor sample, the tumors may not have undergone classification by traditional pathology techniques, may have been initially classified but confirmation is desired, or have been classified as a "carcinoma of unknown primary" (CUP) or "tumor of unknown origin" (TUO) or "unknown primary tumor". The need for confirmation is particularly relevant in light of the estimates of 5 to 10% misclassification using standard techniques. Thus the disclosure may be viewed as providing means for cancer identification, or CID, of a tumor or tumor sample as being one of a plurality of possible tumor types. The range of possible tumor types is disclosed herein, and includes tumor types that were not previously assignable to a unknown cancer or tumor type.

In a first aspect of the disclosure, the classification is performed by use of gene expression profiles, or patterns, of 5 or more, or optionally 50 or more, expressed sequences. The gene expression profiles, whether embodied in nucleic acid expression, protein expression, or other markers of gene expression, may be used to determine a cell containing sample as containing tumor cells of a tissue type or from a tissue origin to permit a more accurate identification of the cancer and thus treatment thereof as well as the prognosis of the subject from whom the sample was obtained.

The expression products of the expressed sequences may be found in multiple tumor types within a plurality, or group, of known possible tumor types as disclosed herein. The expression levels of the sequences may thus occur in more than one tumor type in the group. Additionally, the range of expression levels may overlap between known tumor types in the group. The disclosed methodology of classifying or identifying tumor types may also be applied to the classification or identification of tissue source of cell, such as a tumor or cancer cell.

The classification or identification may be performed by the comparison of gene expression profiles, or patterns, of 50 or more, or optionally 5 or more, expressed sequences in a tumor sample to the expression of the same expressed sequences in a plurality of known tumor types. At least one of the sequences is expressed in more than one of the known tumor types in the plurality of known tumor types. Optionally, the range of expression levels of the at least one sequence in one known tumor type overlaps with the range of expression levels of the same sequence in one or more other known tumor types in the plurality. In some cases, the overlap occurs with 5% or more, 10% or more, 15% or more, 20% or more, 25% or more, 30% or more, 35% or more, 40% or more, 45% or more, or 50% or more of the other known tumor types in the plurality.

In some embodiments, two or more, three or more, four or more, five or more, 10 or more, 15 or more, 20 or more, 25 or more, 30 or more, 35 or more, 40 or more, 45 or more, 50 or more, 55 or more, 60 or more, or a majority of the expressed sequences are expressed in more than one of the known tumor types. Optionally, the range of expression levels of each of the commonly expressed sequences in one known tumor type overlaps with the range of expression levels of the same sequence in one or more other known tumor types in the plurality as described above.

In some embodiments, the disclosure is used to classify among a group of 54 known tumor or cancer types as a plurality. The classification may be performed with significant accuracy in a clinical setting. The disclosure is based in part on the surprising and unexpected discovery that 50 or more expressed sequences in the human genome are capable of classifying among 54 known tumor or cancer types, as well as subsets of those tumor types, in a meaningful manner. Additionally, five to 49 of the expressed sequences may be used to classify among subsets of the 54 known tumor or cancer types.

The disclosure is based in part on the discovery that it is not necessary to use supervised learning to identify gene sequences which are expressed in correlation with different tumor types. Thus the disclosure is based in part on the recognition that the expression levels of any 50 or more expressed sequences, even a random collection of expressed sequences, contains the information content necessary to classify, and so may be used to classify, a cell as being a tumor cell from a plurality or group of known tissues or tissue origins.

In another aspect, the disclosure provides for the classifying of a cell containing sample as containing a tumor cell of a tissue type or origin by determining the expression levels of 5 or more, or optionally 50 or more, transcribed sequences and comparing the expression levels to that of the same transcribed sequences in a plurality or group of known tumor tissue types to classify the cell containing sample as containing a cancer (or tumor) cell of type among the plurality of cancer (or tumor) types. To classify among 54 known cancer types, and subsets thereof, as few as any 5 or more, or optionally 50 or more, expressed sequences may be used for classification in a meaningful manner. The disclosure is also based in part on the observation that the expressed sequences need not only be those with expression levels that are evidently or highly correlated (directly, or indirectly through correlation with another expressed sequence) with one or more of the known tumor types as compared to other known tumors. Thus the disclosure provides, in a further embodiment, for the use of the expression levels of genes that are not expressed in strong or high correlation with one or more of the known tumor types for comparison to a tumor or cancer sample. In some cases, all of the genes used for classification may be non-correlates, or only a portion of the genes may be non-correlates. In some embodiments, at least 90%, 85%, 75%, 50% or 25% of the expression levels used are non-correlated with one or more of the known tumor types.

The disclosure may be practiced by assessing the expression levels of gene sequences where the sequences need not have been selected based on a correlation of their expression levels with members of a plurality of known cancer or tumor types. Thus as a non-limiting example, the gene sequences need not be selected based on their correlation values with cancer or tumor types or a ranking based on the correlation values. Additionally, the disclosure may be practice with use of gene expression levels which are not necessarily correlated to one or more other gene expression level(s) used for classification. So in additional embodiments, the ability for the expression level of one expressed sequence to function in classification is not redundant with (is independent of) the ability of at least one other gene expression level used for classification.

The disclosure may be applied to identify the origin of a cancer in a patient in a wide variety of cases including, but not limited to, identification of the origin of a cancer in a clinical setting. In some embodiments, the identification is made by classification of a cell containing sample known to contain cancer cells, but the origin of those cells is unknown. In other embodiments, the identification is made by classification of a cell containing sample as containing one or more cancer cells followed by identification of the origin(s) of those cancer cell(s). In further embodiments, the disclosure is practiced with a sample from a subject with a previous history of cancer, and identification is made by classification of a cell as either being cancer from a previous origin of cancer or a new origin. Additional embodiments include those where multiple cancers are present in the same organ or tissue, and the disclosure is used to determine the origin of each cancer, as well as whether the cancers are of the same origin.

The disclosure is also based in part on the discovery that the expression levels of particular gene sequences can be used to classify among tumor types with greater accuracy than the expression levels of a random group of gene sequences. In one embodiment, the disclosure provides for the use of expression levels of a disclosed set of expressed sequences in the human genome to classify among known 54 cancer types with significant accuracy. The disclosure thus provides for the identification and use of gene expression patterns (or profiles or "signatures") based on the expressed sequences as having information that may be used to identify the origin of the 54 cancer types. The disclosure also provides for the use of expression levels of these expressed sequences to classify among subsets of the 54 cancer types. Additionally, the disclosure provides for the use of the expression levels of subsets (such as 5 or more) of the disclosed expressed sequences to classify among subsets of the 54 cancer types. Depending on the number of tumor types, accuracies ranging from over 80% to 100% may be achieved.

The disclosure is based upon the expression levels of the gene sequences in a set of known tumor cells from different tissues and of different tumor types. These gene expression profiles (of gene sequences in the different known tumor cells/types), whether embodied in nucleic acid expression, protein expression, or other expression formats, may be compared to the expression levels of the same sequences in an unknown tumor sample to identify the sample as containing a tumor of a particular known type and/or a particular known origin or cell type. The disclosure provides, such as in a clinical setting, the advantages of a more accurate identification of a cancer and thus the treatment thereof as well as the prognosis, including survival and/or likelihood of cancer recurrence following treatment, of the subject from whom the sample was obtained.

The disclosure is also based in part on the discovery that use of 5 or more, or optionally 50 or more, expressed sequences as described herein as capable of classifying among two or more known tumor types necessarily and effectively eliminates one or more known tumor types from consideration during classification. This reflects the lack of a need to select genes with expression levels that are highly correlated with all tumor types within the range of the classification system. Stated differently, the disclosure may be practiced with a plurality of genes the expression levels of which are not highly correlated with any of the individual tumor types or multiple types in the group of tumor types being classified. This is in contrast to other approaches based upon the selection and use of highly correlated genes, which likely do not "rule out" other tumor types as opposed to "rule in" a tumor type based on the positive correlation.

The classification of a tumor sample as being one of the possible cancer types described herein to the exclusion of one or more other cancer types is of course made based upon a level of confidence as described below. Where the level of confidence is low, or an increase in the level of confidence is preferred, the classification can simply be made at the level of a particular tissue origin or cell type for the cancer in the sample. Alternatively, and where a tumor sample is not readily classified as a single tumor type, the disclosure permits the classification of the sample as one of a few possible cancer types described herein. This advantageously provides for the ability to reduce the number of possible tissue types, cell types, and tumor types from which to consider for selection and administration of therapy to the patient from whom the sample was obtained.

The disclosure provides a non-subjective means for the identification of the tissue source and/or cancer type of one or more cancers of an afflicted subject. Where subjective interpretation may have been previously used to determine the tissue source and/or cancer type, as well as the prognosis and/or treatment of the cancer based on that determination, the present disclosure provides objective gene expression patterns, which may used alone or in combination with subjective criteria to provide a more accurate identification of cancer classification. The disclosure is particularly advantageously applied to samples of secondary or metastasized tumors, but any cell containing sample (including a primary tumor sample) for which the tissue source and/or tumor type is preferably determined by objective criteria may also be used with the disclosure. Of course the ultimate determination of class may be made based upon a combination of objective and non-objective (or subjective/partially subjective) criteria.

The disclosure includes its use as part of the clinical or medical care of a patient. Thus in addition to using an expression profile of genes as described herein to assay a cell containing sample from a subject afflicted with cancer to determine the tissue source and/or tumor type of the cancer, the profile may also be used as part of a method to determine the prognosis of the cancer in the subject. The classification of the tumor/cancer and/or the prognosis may be used to select or determine or alter the therapeutic treatment for said subject. Thus the classification methods of the disclosure may be directed toward the treatment of disease, which is diagnosed in whole or in part based upon the classification. Given the diagnosis, administration of an appropriate anti-tumor agent or therapy, or the withholding or alternation of an anti-tumor agent or therapy may be used to treat the cancer.

The details of one or more embodiments of the disclosure are set forth in the accompanying drawing and the description below. Other features and advantages of the disclosure will be apparent from the drawing and detailed description, and from the claims.

DEFINITIONS

As used herein, a "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

A "sequence" or "gene sequence" as used herein is a nucleic acid molecule or polynucleotide composed of a discrete order of nucleotide bases. The term includes the ordering of bases that encodes a discrete product (i.e. "coding region"), whether RNA or proteinaceous in nature. It is appreciated that more than one polynucleotide may be capable of encoding a discrete product. It is also appreciated that alleles and polymorphisms of the human gene sequences may exist and may be used in the practice of the disclosure to identify the expression level(s) of the gene sequences or an allele or polymorphism thereof. Identification of an allele or polymorphism depends in part upon chromosomal location and ability to recombine during mitosis.

An "expressed sequence" is a sequence that is transcribed by cellular processes within a cell. To detect an expressed sequence, a region of the sequence that is unique relative to other expressed sequences may be used. An expressed sequence may encode a polypeptide product or not be known to encode any product. So an expressed sequence may contain open reading frames or no open reading frames. Non-limiting examples include regions of about 8 or more, about 10 or more, about 12 or more, about 14 or more, about 16 or more, about 18 or more, about 20 or more, about 22 or more, about 24 or more, about 26 or more, about 28 or more, or about 30 or more contiguous nucleotides within an expressed sequence may be used. The term "about" as used in the previous sentence refers to an increase or decrease of 1 from the stated numerical value. The physical form of an expressed sequence may be an RNA molecule or the corresponding cDNA molecule.

The terms "correlate" or "correlation" or equivalents thereof refer to an association between expression of one or more genes and another event, such as, but not limited to, physiological phenotype or characteristic, such as tumor type.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence. Methods for amplifying mRNA are generally known in the art, and include reverse transcription PCR (RT-PCR) and quantitative PCR (or Q-PCR) or real time PCR. Alternatively, RNA may be directly labeled as the corresponding cDNA by methods known in the art.

By "corresponding", it is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990), J. Mol. Biol. 215:403-410 (using the published default setting, i.e. parameters w=4, t=17).

A "microarray" is a linear or two-dimensional or three dimensional (and solid phase) array of discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, such as of at least about 50/cm$^2$, at least about 100/cm$^2$, or at least about 500/cm$^2$, up to about 1,000/cm$^2$ or higher. The arrays may contain less than about 500, about 1000, about 1500, about 2000, about 2500, or about 3000 immobilized polynucleotides in total. As used herein, a DNA microarray is an array of oligonucleotide or polynucleotide probes placed on a chip or other surfaces used to hybridize to amplified or cloned polynucleotides from a sample. Since the position of each particular group of probes in the array is known, the identities of a sample polynucleotides can be determined based on their binding to a particular position in the microarray. As an alternative to the use of a microarray, an array of any size may be used in the practice of the disclosure, including an arrangement of one or more position of a two-dimensional or three dimensional arrangement in a solid phase to detect expression of a single gene sequence. In some embodiments, a microarray for use with the present disclosure may be prepared by photolithographic techniques (such as synthesis of nucleic acid probes on the surface from the 3' end) or by nucleic synthesis followed by deposition on a solid surface.

Where the disclosure relies upon the identification of gene expression, some embodiments of the disclosure determine expression by hybridization of mRNA, or an amplified or cloned version thereof, of a sample cell to a polynucleotide that is unique to a particular gene sequence. Polynucleotides of this type contain at least about 16, at least about 18, at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Other embodiments are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Longer polynucleotides may of course contain minor mismatches (e.g. via the presence of mutations) which do not affect hybridization to the nucleic acids of a sample. Such polynucleotides may also be referred to as polynucleotide probes that are capable of hybridizing to sequences of the genes, or unique portions thereof, described herein. Such polynucleotides may be labeled to assist in their detection. The sequences may be those of mRNA encoded by the genes, the corresponding cDNA to such mRNAs, and/or amplified versions of such sequences. In some embodiments of the disclosure, the polynucleotide probes are immobilized on an array, other solid support devices, or in individual spots that localize the probes.

In other embodiments of the disclosure, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing sequences) of the disclosure under conditions which allow for their hybridization. Additional methods to detect the expression of expressed nucleic acids include RNAse protection assays, including liquid phase hybridizations, and in situ hybridization of cells.

Alternatively, and in further embodiments of the disclosure, gene expression may be determined by analysis of expressed protein in a cell sample of interest by use of one or more antibodies specific for one or more epitopes of individual gene products (proteins), or proteolytic fragments thereof, in said cell sample or in a bodily fluid of a subject. The cell sample may be one of breast cancer epithelial cells enriched from the blood of a subject, such as by use of labeled antibodies against cell surface markers followed by fluorescence activated cell sorting (FACS). Such antibodies may be labeled to permit their detection after binding to the gene product. Detection methodologies suitable for use in the practice of the disclosure include, but are not limited to, immunohistochemistry of cell containing samples or tissue, enzyme linked immunosorbent assays (ELISAs) including antibody sandwich assays of cell containing tissues or blood samples, mass spectroscopy, and immuno-PCR.

The terms "label" or "labeled" refer to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

"Expression" and "gene expression" include transcription and/or translation of nucleic acid material. Expression levels of an expressed sequence may optionally be normalized by reference or comparison to the expression level(s) of one or more control expressed genes. These "normalization genes" have expression levels that are relatively constant in all members of the plurality or group of known tumor types.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present disclosure is based on the relative level of gene expression, mutations in non-coding regions of genes as disclosed herein may also be assayed in the practice of the disclosure.

"Detection" or "detecting" includes any means of detecting, including direct and indirect determination of the level of gene expression and changes therein.

Unless defined otherwise all technical and scientific terms used herein have the same meaning as commonly understood to one of ordinary skill in the art to which this disclosure belongs.

DETAILED DESCRIPTION OF MODES OF PRACTICING THE DISCLOSURE

This disclosure provides methods for the use of gene expression information to classify cancers and/or tumors in a more objective manner than possible with conventional pathology techniques. The disclosure is based in part on the results of randomly reducing the number of gene sequences used to classify a tumor sample as one of a plurality of tumor types, such as the tumor types described below and in U.S. Patent Publications US 2006/0094035 and US 2007/0020655. A total number of 16,948 genes, which were filtered down from a larger set based upon removal of genes that display low or constant signals in the samples used was used for both cross-validation and prediction accuracies as described herein.

Thus in a first aspect, the disclosure provides a method of classifying a cell containing sample as including a cancer or tumor cell of (or from) a type of tissue (or as being of a tissue origin). The method comprises determining or measuring the expression levels of 5 or more, or optionally 50 or more, transcribed sequences from cells in a cell containing sample obtained from a subject, and classifying the sample as containing tumor cells of a type of tissue from a plurality of tumor types based on the expression levels of said sequences in the cells of the sample in comparison to expression levels in known tumors. As used herein, "a plurality" refers to the state of two or more.

The classifying is based upon a comparison of the expression levels of the assayed transcribed sequences in the cells of the sample to their expression levels in known tumor samples and/or known non-tumor samples. Alternatively, the classifying is based upon a comparison of the expression levels of the assayed transcribed sequences to the expression of reference sequences in the same samples, relative to, or based on, the same comparison in known tumor samples and/or known non-tumor samples. So as a non-limiting example, the expression levels of the gene sequences may be determined in a set of known tumor samples to provide a database against which the expression levels detected or determined in a cell containing sample from a subject is compared. The expression level(s) of gene sequence(s) in a sample also may be compared to the expression level(s) of said sequence(s) in normal or non-cancerous cells, preferably from the same sample or subject. As described below and in embodiments of the disclosure utilizing Q-PCR or real time Q-PCR, the expression levels may be compared to expression levels of reference genes in the same sample or a ratio of expression levels may be used.

The selection of expressed sequences to use may be random, or by selection based on various criteria. As one non-limiting example, the gene sequences may be selected based upon unsupervised learning, including clustering techniques. As another non-limiting example, selection may be to reduce or remove redundancy with respect to their ability to classify tumor type. For example, gene sequences are selected based upon the lack of correlation between their expression and the expression of one or more other gene sequences used for classifying. This is accomplished by assessing the expression level of each gene sequence in the expression data set for correlation, across the plurality of samples, with the expression level of each other gene in the data set to produce a correlation matrix of correlation coefficients. These correlation determinations may be performed directly, between expression of each pair of gene sequences, or indirectly, without direct comparison between the expression values of each pair of gene sequences.

A variety of correlation methodologies may be used in the correlation of expression data of individual gene sequences within the data set. Non-limiting examples include parametric and non-parametric methods as well as methodologies based on mutual information and non-linear approaches. Non-limiting examples of parametric approaches include Pearson correlation (or Pearson r, also referred to as linear or product-moment correlation) and cosine correlation. Non-limiting examples of non-parametric methods include Spearman's R (or rank-order) correlation, Kendall's Tau correlation, and the Gamma statistic. Each correlation methodology can be used to determine the level of correlation between the expressions of individual gene sequences in the data set. The correlation of all sequences with all other sequences is most readily considered as a matrix. Using Pearson's correlation as a non-limiting example, the correlation coefficient r in the method is used as the indicator of the level of correlation. When other correlation methods are used, the correlation coefficient analogous to r may be used, along with the recognition of equivalent levels of correlation corresponding to r being at or about 0.25 to being at or about 0.5.

The correlation coefficient may be selected as desired to reduce the number of correlated gene sequences to various numbers. In some embodiments of the disclosure using r, the selected coefficient value may be of about 0.25 or higher, about 0.3 or higher, about 0.35 or higher, about 0.4 or higher, about 0.45 or higher, or about 0.5 or higher. The selection of a coefficient value means that where expression between gene sequences in the data set is correlated at that value or higher, they are possibly not included in a subset of the disclosure. Thus in some embodiments, the method comprises excluding or removing (not using for classification) one or more gene sequences that are expressed in correlation, above a desired correlation coefficient, with another gene sequence in the tumor type data set. It is pointed out, however, that there can be situations of gene sequences that are not correlated with any other gene sequences, in which case they are not necessarily removed from use in classification.

Thus the expression levels of gene sequences, where more than about 10%, more than about 20%, more than about 30%, more than about 40%, more than about 50%, more than about 60%, more than about 70%, more than about 80%, or more than about 90% of the levels are not correlated with that of another one of the gene sequences used, may be used in the practice of the disclosure. Correlation between expression levels may be based upon a value below about 0.9, about 0.8, about 0.7, about 0.6, about 0.5, about 0.4, about 0.3, or about 0.2. The ability to classify among classes with exclusion of the expression levels of some gene sequences is present because expression of the gene sequences in the subset is correlated with expression of the gene sequences excluded from the subset. So no information was lost because information based on the expression of the excluded gene sequences is still represented by sequences retained in the subset. Therefore, expression of the gene sequences of the subset has information content relevant to properties and/or characteristics (or phenotype) of a cell. This has application and relevance to the classification of additional tumor type classes not included as part of the original gene expression data set which can be classified by use of a subset of the disclosure because based on the redundancy of information between expression of sequences in the subset and sequences expressed in those additional classes. Thus the disclosure may be used to classify cells as being a tumor type beyond the plurality of known classes used to generate the original gene expression data set.

Selection of gene sequences based upon reducing correlation of expression to a particular tumor type may also be used. This also reflects a discovery of the present disclosure, based upon the observation that expression levels that were most highly correlated with one or more tumor types was not necessarily of greatest value in classification among different tumor types. This is reflected both by the ability to use randomly selected gene sequences for classification as well as the use of particular sequences, as described herein, which are not expressed with the most significant correlation with one or more tumor types. Thus the disclosure may be practiced without selection of gene sequences based upon the most significant P values or a ranking based upon correlation of gene expression and one or more tumor types. Thus the disclosure may be practiced without the use of ranking based methodologies, such as the Kruskal-Wallis H-test.

The gene sequences used in the practice of the disclosure may include those which have been observed to be expressed in correlation with particular known tumor types, such as expression of the estrogen receptor, which has been observed to be expressed in correlation with some breast and ovarian cancers. In some embodiments of the disclosure, however, the disclosure is practiced with use of expression levels of multiple gene sequences where the expression levels overlap in two or more of the known tumor types. In some cases, one or more of the transcribed sequences have expression levels that overlap in all of the known tumor types, at least 50 of the known tumor types, at least 45 of the known tumor types, at least 40 of the known tumor types, at least 35 of the known tumor types, at least 30 of the known tumor types, at least 25 of the known tumor types, at least 20 of the known tumor types, at least 10 of the known tumor types, or at least 5 of the known tumor types of a disclosed group.

Used in the practice of the disclosed methods, the number of transcribed sequences that are expressed with a range of overlapping levels in two or more known tumor types of a disclosed group may be 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 22 or more, 24 or more, 26 or more, 28 or more, 30 or more, 32 or more, 34 or more, 36 or more, 38 or more, 40 or more, 42 or more, 44 or more, 46 or more, 48 or more, 50 or more, 52 or more, 54 or more, 56 or more, 58 or more, 60 or more, 62 or more, 64 or more, 66 or more, 68 or more, 70 or more, 72 or more, 74 or more, 76 or more, 78 or more, 80 or more, 92 or more, 94 or more, 96 or more, 98 or more, 100 or more, 105 or more, 110 or more, 120 or more, 130 or more, 140 or more, or 150 or more. Of course the above values may be used with one or more transcribed sequences with expression levels that do not overlap between two, or more, members of a group of known tumor types. Based upon the number of known tumor types in a plurality, skilled person may practice the disclosure any appropriate combination of a number of tumor types with overlapping expression of the sample transcribed sequences and a number of transcribed sequences with overlapping expression levels in two or more tumor types.

While the disclosure is described mainly with respect to human subjects, samples from other subjects may also be used. All that is necessary is the ability to assess the expression levels of gene sequences in a plurality of known tumor samples such that the expression levels in an unknown or test sample may be compared. Thus the disclosure may be applied to samples from any organism for which a plurality of expressed sequences, and a plurality of known tumor samples, are available. One non-limiting example is application of the disclosure to mouse samples, based upon the availability of the mouse genome to permit detection of expressed murine sequences and the availability of known mouse tumor samples or the ability to obtain known samples. Thus, the disclosure is contemplated for use with other samples, including those of mammals, primates, and animals used in clinical testing (such as rats, mice, rabbits, dogs, cats, and chimpanzees) as non-limiting examples.

While the disclosure is readily practiced with the use of cell containing samples, any nucleic acid containing sample which may be assayed for gene expression levels may be used in the practice of the disclosure. Without limiting the disclosure, a sample of the disclosure may be one that is suspected or known to contain tumor cells. Alternatively, a sample of the disclosure may be a "tumor sample" or "tumor containing sample" or "tumor cell containing sample" of tissue or fluid isolated from an individual suspected of being afflicted with, or at risk of developing, cancer. Non-limiting examples of samples for use with the disclosure include a clinical sample, such as, but not limited to, a fixed sample, a fresh sample, or a frozen sample. The sample may be an aspirate, a cytological sample (including blood or other bodily fluid, including fluid from an ascites or a pleural cavity), or a tissue specimen, which includes at least some information regarding the in situ context of cells in the specimen, so long as appropriate cells or nucleic acids are available for determination of gene expression levels. The disclosure is based in part on the discovery that results obtained with frozen tissue sections can be validly applied to the situation with fixed tissue or cell samples and extended to fresh samples.

Non-limiting examples of fixed samples include those that are fixed with formalin or formaldehyde (including FFPE samples), with Boudin's, glutaldehyde, acetone, alcohols, or any other fixative, such as those used to fix cell or tissue samples for immunohistochemistry (IHC). Other examples include fixatives that precipitate cell associated nucleic acids and proteins. Given possible complications in handling frozen tissue specimens, such as the need to maintain its frozen state, the disclosure may be practiced with non-frozen samples, such as fixed samples, fresh samples, including cells from blood or other bodily fluid or tissue, and minimally treated samples. In some applications of the disclosure, the sample has not been classified using standard pathology techniques, such as, but not limited to, immunohistochemistry based assays.

In some embodiments of the disclosure, the sample is classified as containing a tumor cell of a type selected from the following 54, and subsets thereof: adrenal-cortical tumor, adrenal pheochromocytoma, tumor of the brain, adenocarcinoma of breast, cervical adenocarcinoma, cervical squamous cell carcinoma, cholangiocarcinoma, endometrial adenocarcinoma, esophageal squamous cell carcinoma, gastrointestinal stromal tumor, adenocarcinoma of gallbladder, gastro-esophageal adenocarcinoma, seminomatous germ cell tumor, nonseminomatous germ cell tumor, tumor of the salivary gland, squamous cell carcinoma, colorectal adenocarcinoma, small intestine adenocarcinoma, clear cell renal cell carcinoma, chromophobe renal cell carcinoma, papillary renal cell carcinoma, hepatocellular carcinoma, lung adenocarcinoma, lung squamous cell carcinoma, lymphoma, melanoma, meningioma, mesothelioma, small/large cell neuroendocrine lung cancer, neuroendocrine-pancreas cancer, merkel cell carcinoma, gastrointestinal carcinoid, lung carcinoid, clear cell adenocarinoma, endometrioid adenocarcinoma, mucinous adenocarcinoma, serous adenocarcinoma, pancreatic adenocarcinoma, prostate adenocarcinoma, malignant fibrous histiocytoma, primitive neuroectodermal tumor, leiomyosarcoma, liposarcoma, osteosarcoma, synovial sarcoma, sex cord stromal tumor, basal cell carcinoma, skin squamous cell carcinoma, thymic carcinoma/thymoma, follicular/papillary carcinoma, medullary carcinoma, transitional cell carcinoma, adenocarcinoma of bladder, and squamous cell carcinoma of bladder.

These 54 tumor types correspond to the following tissue types: adrenal tissue (adrenal-cortical tumor and adrenal pheochromocytoma), brain tissue (tumor of the brain), breast tissue (adenocarcinoma of breast), cervical tissue (cervical adenocarcinoma and cervical squamous cell carcinoma), bile duct tissue (cholangiocarcinoma), endometrial tissue (endometrial adenocarcinoma), esophageal tissue (esophageal squamous cell carcinoma), gastrointestinal tissue (gastrointestinal stromal tumor or GIST), gall bladder tissue (adenocarcinoma of gall bladder), gastro-esophageal tissue (gastro-esophageal adenocarcinoma), germ cell tissue (seminomatous germ cell tumor and nonseminomatous germ cell tumor), head and neck tissue (tumor of the salivary gland and squamous cell carcinoma), intestinal tissue (colorectal adenocarcinoma and small intestine adenocarcinoma), kidney tissue (clear cell renal cell carcinoma, chromophobe renal cell carcinoma, and papillary renal cell carcinoma), liver tissue (hepatocellular carcinoma), lung tissue (lung adenocarcinoma and lung squamous cell carcinoma), lymphocytes (lymphoma), melanocytes (melanoma), meningeal tissue (meningioma), tissue of a mesothelium (mesothelioma), neuroendocrine tissue (small/large cell neuroendocrine lung cancer, neuroendocrine-pancreas cancer, merkel cell carcinoma, gastrointestinal carcinoid, and lung carcinoid), ovary tissue (clear cell adenocarinoma, endometrioid adenocarcinoma, mucinous adenocarcinoma, and serous adenocarcinoma), tissue of the pancreas (pancreatic adenocarcinoma), prostate tissue (prostate adenocarcinoma), tissue of a sarcoma (malignant fibrous histiocytoma or MFH, primitive neuroectodermal tumor or PNET, leiomyosarcoma, liposarcoma, osteosarcoma, and synovial sarcoma), sex cord stromal tissue (sex cord stromal tumor), skin tissue (basal cell carcinoma and skin squamous cell carcinoma), thymus tissue (thymic carcinoma/thymoma), thyroid tissue (follicular/papillary carcinoma and medullary carcinoma), and urinary bladder tissue (transitional cell carcinoma, adenocarcinoma of bladder, and squamous cell carcinoma of bladder).

The methods of the disclosure may also be applied to classify a cell containing sample as containing a tumor cell of a tumor of a subset of any of the above-listed types. The size of the subset may be small, composed of two, three, four, five, six, seven, eight, nine, or ten of the tumor types described above. Alternatively, the size of the subset may be any integral number up to the full size of the set. Thus embodiments of the disclosure include classification among 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 of the above types. In some embodiments, the subset will be composed of tumor types that are of the same tissue or organ type. Alternatively, the subset will be composed of tumor types of different tissues or organs. It cannot be overemphasized that the disclosure is not based upon any particular combination of tumor types and that all possible combinations of the above 54 known types are expressly contemplated as embodiments of the disclosure. The finite possibility of explicitly writing out all combinations of the 54 tumor types would be to require an arbitrary form over the substance of the discovery and disclosure.

While classification among some subsets of the above tumor types has been reported in U.S. Patent Publications US 2006/0094035 and US 2007/0020655 as well as Ma et al. (*Arch. Pathol. Lab. Med.*, 130:465-473, 2006), it is believed that the instant disclosure is the first regarding successful identification of at least adrenal-cortical tumor, tumor of the salivary gland, squamous cell carcinoma, neuroendocrine-pancreas cancer, merkel cell carcinoma, lung carcinoid, primitive neuroectodermal tumor, sex cord stromal tumor, thymic carcinoma/thymoma, adenocarcinoma of urinary bladder, and squamous cell carcinoma of urinary bladder. Therefore, and in some embodiments, a group of known tumor types would include one or more types from this list.

The disclosure may be practiced with the expression levels of about 10 or more, about 15 or more, about 20 or more, about 25 or more, about 30 or more, about 35 or more, about 40 or more, about 45 or more, or about 50 or more transcribed sequences as found in the human "transcriptome" (transcribed portion of the genome). In some embodiments of the disclosure, the transcribed genes may be randomly picked or include all or some of the specific genes sequences disclosed herein. Classification with accuracies of about 55%, about 60%, about 65%, about 70%, about 75%, about 80%, about 85%, about 90%, or about 95% or higher can be performed by use of the instant disclosure.

In other embodiments, the gene expression levels of other gene sequences may be determined along with the above described determinations of expression levels for use in classification. One non-limiting example of this is seen in the case of a microarray based platform to determine gene expression, where the expression of other gene sequences is also measured. Where those other expression levels are not used in comparison to expression in known tumor types, they may be considered the results of "excess" transcribed sequences and not critical to the practice of the disclosure. Alternatively, and where those other expression levels are used in classification, they are within the scope of the disclosure, where the description of using particular numbers of sequences does not necessarily exclude the use of expression levels of additional sequences. In some embodiments, the disclosure includes the use of expression level(s) from one or more "excess" gene sequences, such as those which may provide information redundant to one or more other gene sequences used in a method of the disclosure.

Because classification of a sample as containing cells of one of the above tumor types inherently also classifies the tissue or organ site origin of the sample, the methods of the disclosure may be applied to classification of a tumor sample as being of a particular tissue or organ site of a subject from which the sample was obtained. This application of the disclosure is particularly useful in cases where the sample is of a tumor that is the result of metastasis by another tumor. In some embodiments of the disclosure, the tumor sample is classified as being one of the following 30 known tissue types: adrenal tissue, brain tissue, breast tissue, cervical tissue, bile duct tissue, endometrial tissue, esophageal tissue, gastrointestinal tissue, gall bladder tissue, gastro-esophageal tissue, germ cell tissue, head and neck tissue, intestinal tissue, kidney tissue, liver tissue, lung tissue, lymphocytes, melanocytes, meningeal tissue, tissue of a mesothelium, neuroendocrine tissue, ovary tissue, tissue of the pancreas, prostate tissue, tissue of a sarcoma, sex cord stromal tissue, skin tissue, thymus tissue, thyroid tissue, and urinary bladder tissue.

The classification of a cell containing sample as having a tumor cell of one of the disclosed 54 tumor types above inherently also classifies the tissue or organ site origin of the sample. For example, the identification of a sample as being cervical squamous cell carcinoma necessarily classifies the tumor as being of cervical origin, squamous cell type (and thus epithelial rather than non-epithelial in origin). It also means that the tumor was necessarily not germ cell in origin. Thus, the methods of the disclosure may be applied to classification of a tumor sample as being of a particular tissue or organ site of a subject or patient. This application of the disclosure is particularly useful in cases where the sample is of a tumor that is the result of metastasis by another tumor.

The practice of the disclosure to classify a cell containing sample as having a tumor cell of one of the above types is by use of an appropriate classification algorithm that utilizes supervised learning to accept 1) the levels of expression of the gene sequences in a plurality of known tumor types as a training set and 2) the levels of expression of the same genes in one or more cells of a sample to classify the sample as having cells of one of the tumor types. Such algorithms are known to the skilled person and have been described elsewhere. The levels of expression may be provided based upon the signals in any format, including nucleic acid expression or protein expression as described herein.

Embodiments of the disclosure include use of the methods and materials described herein to identify the origin of a cancer from a patient. Thus given a sample containing tumor cells, the tissue origin of the tumor cells is identified by use of the present disclosure. One non-limiting example is in the case of a subject with an inflamed lymph node containing cancer cells. The cells may be from a tissue or organ that drains into the lymph node or it may be from another tissue source. The present disclosure may be used to classify the cells as being of a particular tumor or tissue type (or origin) which allows the identification of the source of the cancer cells. In an alternative non-limiting example, the sample (such as that from a lymph node) contains cells, which are first assayed by use of the disclosure to classify at least one cell as being a tumor cell of a tissue type or origin. This is then used to identify the source of the cancer cells in the sample. Both of these are examples of the advantageous use of the disclosure to save time, effort, and cost in the use of other cancer diagnostic tests.

In further embodiments, the disclosure is practiced with a sample from a subject with a previous history of cancer. As a non-limiting example, a cell containing sample (from the lymph node or elsewhere) of the subject may be found to contain cancer cells such that the present disclosure may be used to determine whether the cells are from the same or a different tissue from that of the previous cancer. This application of the disclosure may also be used to identify a new primary tumor, such as the case where new cancer cells are found in the liver of a subject who previously had breast cancer. The disclosure may be used to identify the new cancer cells as being the result of metastasis from the previous breast cancer (or from another tumor type, whether previously identified or not) or as a new primary occurrence of liver cancer. The disclosure may also be applied to samples of a tissue or organ where multiple cancers are found to determine the origin of each cancer, as well as whether the cancers are of the same origin.

While the disclosure may be practiced with the use of expression levels of a random group of expressed gene sequences, the disclosure also provides exemplary gene sequences for use in the practice of the disclosure. The disclosure includes a group of 87 gene sequences from which 5 or more may be used in the practice of the disclosure. The gene sequences may be used along with the determination of expression levels of additional sequences so long as the expression levels of gene sequences from the set of 87 are used in classifying. A non-limiting example of such embodiments of the disclosure is where the expression of from 5 or more of the 87 gene sequences is measured along with the expression levels of a plurality of other sequences, such as by use of a microarray based platform used to perform a disclosed method. Where those other expression levels are not used in classification, they may be considered the results of "excess" transcribed sequences and optional to the practice of the disclosure. Alternatively, and where those other expression levels are used in classification, they are within the scope of the disclosure, where the use of the above described sequences does not necessarily exclude the use of expression levels of additional sequences.

Representative, and non-limiting, mRNA sequences corresponding to a set of 87 gene sequences for use in the practice of the disclosure have been previously reported in U.S. Patent Publications US 2006/0094035 and US 2007/0020655. The listing of identifying information, including accession numbers, Gene Symbols, and Description, is provided by the following table, where ATF indicates ascites tumor fluid, EGF is epidermal growth factor, and CLL is chronic lymphatic leukemia:

| Accession | Gene Symbol | Description* |
|---|---|---|
| AA456140 | PANX3 | Pannexin 3 |
| AA745593 | BATF | Basic leucine zipper transcription factor, ATF-like |
| AA765597 | SPRED2 | Sprouty-related, EVH1 domain containing 2 |
| AA782845 | SLC35F3 | Solute carrier family 35, member F3 |
| AA865917 | | Hypothetical LOC389142 |
| AA946776 | FGF9 | Fibroblast growth factor 9 (glia-activating factor) |
| AA993639 | FLJ10748 | Hypothetical protein FLJ10748 |
| AB038160 | TMPRSS3 | Transmembrane protease, serine 3 |
| AF104032 | SLC7A5 | Solute carrier family 7 (cationic amino acid transporter, y+ system), member 5 |
| AF133587 | RTDR1 | Rhabdoid tumor deletion region gene 1 |
| AF301598 | EMX2 | Empty spiracles homolog 2 (*Drosophila*) |
| AF332224 | CYorf15A | Chromosome Y open reading frame 15A |
| AI041545 | KDELR2 | KDEL (Lys-Asp-Glu-Leu) endoplasmic reticulum protein retention receptor 2 |
| AI147926 | CSF2RB | Colony-stimulating factor 2 receptor, beta, low-affinity (granulocyte-macrophage) |
| AI309080 | KCNJ11 | Potassium inwardly rectifying channel, subfamily J, member 11 |
| AI341378 | CPEB2 | Cytoplasmic polyadenylation element binding protein 2 |
| AI457360 | ERN2 | Endoplasmic reticulum to nucleus signalling 2 |

| Accession | Gene Symbol | Description* |
|---|---|---|
| AI620495 | MEIS1 | Meis1, myeloid ecotropic viral integration site 1 homolog (mouse) |
| AI632869 | UPK1B | Uroplakin 1B |
| AI683181 | PRDM6 | PR domain containing 6 |
| AI685931 | KIBRA | KIBRA protein |
| AI802118 | SLC6A13 | Solute carrier family 6 (neurotransmitter transporter, GABA), member 13 |
| AI804745 | | |
| AI952953 | | |
| AI985118 | C14orf105 | Chromosome 14 open reading frame 105 |
| AJ000388 | CAPN6 | Calpain 6 |
| AK025181 | LOC91464 | RAX-like homeobox |
| AK027147 | TITF1 | Hypothetical protein LOC253970 |
| AK054605 | FLJ11539 | Hypothetical protein FLJ11539 |
| AL023657 | SH2D1A | SH2 domain protein 1A, Duncan disease (lymphoproliferative syndrome) |
| AL039118 | FOXG1B | Forkhead box G1A |
| AL110274 | | |
| AL157475 | C8orf13 | Chromosome 8 open reading frame 13 |
| AW118445 | CELSR2 | Cadherin, EGF LAG seven-pass G-type receptor 2 (flamingo homolog, *Drosophila*) |
| AW194680 | HOXD11 | Homeobox D11 |
| AW291189 | | Hypothetical LOC388416 |
| AW298545 | KIAA1904 | KIAA1904 protein |
| AW445220 | LY6K | Lymphocyte antigen 6 complex, locus K |
| AW473119 | ESR1 | Estrogen receptor 1 |
| AY033998 | ELAVL4 | ELAV (embryonic lethal, abnormal vision, *Drosophila*)-like 4 (Hu antigen D) |
| BC000045 | VGLL1 | Vestigial like 1 (*Drosophila*) |
| BC001293 | HOXC10 | Homeobox C10 |
| BC001504 | PYCR1 | Pyrroline-5-carboxylate reductase 1 |
| BC001639 | SLC43A1 | Solute carrier family 43, member 1 |
| BC002551 | CDCA3 | Cell division cycle associated 3 |
| BC004331 | HSDL2 | Hydroxysteroid dehydrogenase like 2 |
| BC004453 | HTR3A | 5-hydroxytryptamine (serotonin) receptor 3A |
| BC005364 | C10orf59 | Chromosome 10 open reading frame 59 |
| BC006537 | HOXA9 | Homeobox A9 |
| BC006881 | PPARG | Peroxisome proliferative activated receptor, gamma |
| BC006819 | S100P | S100 calcium binding protein P |
| BC008764 | KIF2C | Kinesin family member 2C |
| BC008765 | SDC1 | Syndecan 1 |
| BC009084 | SELENBP1 | Selenium binding protein 1 |
| BC009237 | TSHR | Thyroid-stimulating hormone receptor |
| BC010626 | KIF12 | Kinesin family member 12 |
| BC011949 | CA2 | Carbonic anhydrase II |
| BC012926 | EPS8L3 | EPS8-like 3 |
| BC013117 | RGS17 | Regulator of G-protein signalling 17 |
| BC015754 | CADPS | $Ca^{2+}$-dependent secretion activator |
| BC017586 | MGC26610 | Calcyphosine-like |
| BE552004 | | CDNA FLJ44317 fis, clone TRACH3000586 |
| BE962007 | COX11 | COX11 homolog, cytochrome c oxidase assembly protein (yeast) |
| BF224381 | | Hypothetical LOC400951 |
| BF437393 | | |
| BF446419 | PCANAP6 | Prostate cancer-associated protein 6 |
| BF592799 | PRKCQ | Protein kinase C, theta |
| BI493248 | IBSP | Integrin-binding sialoprotein (bone sialoprotein, bone sialoprotein II) |
| H05388 | ZNF365 | Hypothetical protein LOC283045 |
| H07885 | | Transcribed locus |
| H09748 | BCL11B | B-cell CLL/lymphoma 11B (zinc finger protein) |
| M95585 | HLF | Hepatic leukemia factor |
| N64339 | GJB6 | Gap junction protein, beta 6 (connexin 30) |
| NM_000065 | C6 | Complement component 6 |
| NM_001337 | CX3CR1 | Chemokine (C—X3—C motif) receptor 1 |
| NM_003914 | CCNA1 | Cyclin A1 |
| NM_004062 | CDH16 | Cadherin 16, KSP-cadherin |
| NM_004063 | CDH17 | Cadherin 17, LI cadherin (liver-intestine) |
| NM_004496 | FOXA1 | Forkhead box A1 |
| NM_006115 | PRAME | Preferentially expressed antigen in melanoma |
| NM_019894 | TMPRSS4 | Transmembrane protease, serine 4 |
| NM_033229 | TRIM15 | Tripartite motif-containing 15 |
| R15881 | CHRM3 | Cholinergic receptor, muscarinic 3 |
| R45389 | | CDNA clone IMAGE: 4797120 |
| R61469 | | Transcribed locus, moderately similar to NP_775622.1 hypothetical protein LOC270028 [*Mus musculus*] |
| X69699 | PAX8 | Paired box gene 8 |
| X96757 | MAP2K6 | Mitogen-activated protein kinase kinase 6 |

As would be understood by the skilled person, detection of expression of any of the above identified sequences may be performed by the detection of expression of any appropriate portion or fragment of these sequences. Preferably, the portions are sufficiently large to contain unique sequences relative to other sequences expressed in a cell containing sample. Moreover, the skilled person would recognize that the disclosed sequences represent one strand of a double stranded molecule and that either strand may be detected as an indicator of expression of the disclosed sequences. This is because the disclosed sequences are expressed as RNA molecules in cells which are preferably converted to cDNA molecules for ease of manipulation and detection. The resultant cDNA molecules may have the sequences of the expressed RNA as well as those of the complementary strand thereto. Thus either the RNA sequence strand or the complementary strand may be detected. Of course is it also possible to detect the expressed RNA without conversion to cDNA.

In some embodiments of the disclosure, the expression levels of gene sequences is measured by detection of expressed sequences in a cell containing sample as hybridizing to oligonucleotides of the disclosed gene sequences as indicated by the accession numbers provided.

In additional embodiments, the disclosure provides for use of any number of the gene sequences of the set of 87 in the methods of the disclosure. Thus any integral number from 1 to all of the 87 gene sequences may be used in the practice of the disclosure.

As used herein, a "tumor sample" or "tumor containing sample" or "tumor cell containing sample" or variations thereof, refer to cell containing samples of tissue or fluid isolated from an individual suspected of being afflicted with, or at risk of developing, cancer. The samples may contain tumor cells which may be isolated by known methods or other appropriate methods as deemed desirable by the skilled practitioner. These include, but are not limited to, microdissection, laser capture microdissection (LCM), or laser microdissection (LMD) before use in the instant disclosure. Alternatively, undissected cells within a "section" of tissue may be used. Non-limiting examples of such samples include primary isolates (in contrast to cultured cells) and may be collected by any non-invasive or minimally invasive means, including, but not limited to, ductal lavage, fine needle aspiration, needle biopsy, the devices and methods described in U.S. Pat. No. 6,328,709, or any other suitable means recognized in the art. Alternatively, the sample may be collected by an invasive method, including, but not limited to, surgical biopsy.

The detection and measurement of transcribed sequences may be accomplished by a variety of means known in the art or as deemed appropriate by the skilled practitioner. Essentially, any assay method may be used as long as the assay reflects, quantitatively or qualitatively, the level of expression of the transcribed sequence being detected.

The ability to classify tumor samples is provided by the recognition of the relevance of the level of expression of the gene sequences (whether randomly selected or specific) and not by the form of the assay used to determine the actual level of expression. An assay of the disclosure may utilize any identifying feature of a individual gene sequence as disclosed herein as long as the assay reflects, quantitatively or qualitatively, expression of the gene in the "transcriptome" (the transcribed fraction of genes in a genome) or the "proteome" (the translated fraction of expressed genes in a genome). Additional assays include those based on the detection of polypeptide fragments of the relevant member or members of the proteome. Non-limiting examples of the latter include detection of proteolytic fragments found in a biological fluid, such as blood or serum. Identifying features include, but are not limited to, unique nucleic acid sequences used to encode (DNA), or express (RNA), said gene or epitopes specific to, or activities of, a protein encoded by a gene sequence.

Additional means include detection of nucleic acid amplification as indicative of increased expression levels and nucleic acid inactivation, deletion, or methylation, as indicative of decreased expression levels. Stated differently, the disclosure may be practiced by assaying one or more aspect of the DNA template(s) underlying the expression of each gene sequence, of the RNA used as an intermediate to express the sequence, or of the proteinaceous product expressed by the sequence, as well as proteolytic fragments of such products. As such, the detection of the presence of, amount of, stability of, or degradation (including rate) of, such DNA, RNA and proteinaceous molecules may be used in the practice of the disclosure.

In some embodiments, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing gene sequences) of the disclosure under conditions which allow for their hybridization. Additional methods to detect the expression of expressed nucleic acids include RNAse protection assays, including liquid phase hybridizations, and in situ hybridization of cells.

Alternatively, the expression of gene sequences in FFPE samples may be detected as disclosed in U.S. Pat. No. 7,364,846 B2 (which is hereby incorporated by reference as if fully set forth). Briefly, the expression of all or part of an expressed gene sequence or transcript may be detected by use of hybridization mediated detection (such as, but not limited to, microarray, bead, or particle based technology) or quantitative PCR mediated detection (such as, but not limited to, real time PCR and reverse transcriptase PCR) as non-limiting examples. The expression of all or part of an expressed polypeptide may be detected by use of immunohistochemistry techniques or other antibody mediated detection (such as, but not limited to, use of labeled antibodies that bind specifically to at least part of the polypeptide relative to other polypeptides) as non-limiting examples. Additional means for analysis of gene expression are available, including detection of expression within an assay for global, or near global, gene expression in a sample (e.g. as part of a gene expression profiling analysis such as on a microarray).

In embodiments using a nucleic acid based assay to determine expression includes immobilization of one or more gene sequences on a solid support, including, but not limited to, a solid substrate as an array or to beads or bead based technology as known in the art. Alternatively, solution based expression assays known in the art may also be used. The immobilized gene sequence(s) may be in the form of polynucleotides that are unique or otherwise specific to the gene(s) such that the polynucleotides would be capable of hybridizing to the DNA or RNA of said gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the genes is not affected. In some embodiments, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal. Thus the practice of the present disclosure is unaffected by the presence of minor mismatches between the disclosed sequences and those expressed by cells of a subject's sample. A non-limiting example of the existence of such mismatches are seen in cases of sequence polymorphisms between individuals of a species, such as individual human patients within Homo sapiens.

As known by those skilled in the art, some gene sequences include 3' poly A (or poly T on the complementary strand) stretches that do not contribute to the uniqueness of the disclosed sequences. The disclosure may thus be practiced with gene sequences lacking the 3' poly A (or poly T) stretches. The uniqueness of the disclosed sequences refers to the portions or entireties of the sequences which are found only in nucleic acids, including unique sequences found at the 3' untranslated portion thereof. Some unique sequences for the practice of the disclosure are those which contribute to the consensus sequences for the genes such that the unique sequences will be useful in detecting expression in a variety of individuals rather than being specific for a polymorphism present in some individuals. Alternatively, sequences unique to an individual or a subpopulation may be used. The unique sequences may be the lengths of polynucleotides of the disclosure as described herein.

In additional embodiments of the disclosure, polynucleotides having sequences present in the 3' untranslated and/or non-coding regions of gene sequences are used to detect expression levels in cell containing samples of the disclosure. Such polynucleotides may optionally contain sequences found in the 3' portions of the coding regions of gene sequences. Polynucleotides containing a combination of sequences from the coding and 3' non-coding regions preferably have the sequences arranged contiguously, with no intervening heterologous sequence(s).

Alternatively, the disclosure may be practiced with polynucleotides having sequences present in the 5' untranslated and/or non-coding regions of gene sequences to detect the level of expression in cells and samples of the disclosure. Such polynucleotides may optionally contain sequences found in the 5' portions of the coding regions. Polynucleotides containing a combination of sequences from the coding and 5' non-coding regions may have the sequences arranged contiguously, with no intervening heterologous sequence(s). The disclosure may also be practiced with sequences present in the coding regions of gene sequences.

The polynucleotides of some embodiments contain sequences from 3' or 5' untranslated and/or non-coding regions of at least about 16, at least about 18, at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Other embodiments use polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of gene coding regions as found in polynucleotides of the disclosure are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

In another embodiment of the disclosure, polynucleotides containing deletions of nucleotides from the 5' and/or 3' end of gene sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the sequences and the need to be able to use the polynucleotides for the detection of expression levels.

Other polynucleotides of the disclosure from the 3' end of gene sequences include those of primers and optional probes for quantitative PCR. Preferably, the primers and probes are those which amplify a region less than about 750, less than about 700, less than about 650, less than about 6000, less than about 550, less than about 500, less than about 450, less than about 400, less than about 350, less than about 300, less than about 250, less than about 200, less than about 150, less than about 100, or less than about 50 nucleotides from the from the polyadenylation signal or polyadenylation site of a gene or expressed sequence. The size of a PCR amplicon of the disclosure may be of any size, including at least or about 50, at least or about 100, at least about or 150, at least or about 200, at least or about 250, at least or about 300, at least or about 350, or at least or about 400 consecutive nucleotides, all with inclusion of the portion complementary to the PCR primers used.

Other polynucleotides for use in the practice of the disclosure include those that have sufficient homology to gene sequences to detect their expression by use of hybridization techniques. Such polynucleotides preferably have about or 95%, about or 96%, about or 97%, about or 98%, or about or 99% identity with the gene sequences to be used. Identity is determined using the BLAST algorithm, as described above. The other polynucleotides for use in the practice of the disclosure may also be described on the basis of the ability to hybridize to polynucleotides of the disclosure under stringent conditions of about 30% v/v to about 50% formamide and from about 0.01M to about 0.15M salt for hybridization and from about 0.01M to about 0.15M salt for wash conditions at about 55 to about 65° C. or higher, or conditions equivalent thereto.

In a further embodiment of the disclosure, a population of single stranded nucleic acid molecules comprising one or both strands of a human gene sequence is provided as a probe such that at least a portion of said population may be hybridized to one or both strands of a nucleic acid molecule quantitatively amplified from RNA of a cell or sample of the disclosure. The population may be only the antisense strand of a human gene sequence such that a sense strand of a molecule from, or amplified from, a cell may be hybridized to a portion of said population. The population preferably comprises a sufficiently excess amount of said one or both strands of a human gene sequence in comparison to the amount of expressed (or amplified) nucleic acid molecules containing a complementary gene sequence.

The disclosure further provides a method of classifying a human tumor sample by detecting the expression levels of 5 or more, optionally 50 or more, transcribed sequences in a nucleic acid or cell containing sample obtained from a human subject, and classifying the sample as containing a tumor cell of a tumor type found in humans to the exclusion of one or more other human tumor types. In some embodiments, the method may be used to classify a sample as being, or having cells of, one of the 54 tumor types listed above to the exclusion of one or more of the others.

The disclosure also provides a method for classifying tumor samples as being one of a subset of the possible tumor types described herein by detecting the expression levels of 5 or more, or optionally 50 or more, transcribed sequences in a nucleic acid containing tumor sample obtained from a human subject, and classifying the sample as being one of a number of tumor types found in humans to the exclusion of one or more other human tumor types. In some embodiments of the disclosure, the number of other tumor types is from 1 to about 3, more preferably from 1 to about 5, from 1 to about 7, or from 1 to about 9 or about 10. In other embodiments, the tumor types are all of the same tissue or organ origin such as those listed above.

In additional embodiments, the disclosure may be practiced by analyzing gene expression from single cells or homogenous cell populations which have been dissected away from, or otherwise isolated or purified from, contaminating cells of a sample as present in a simple biopsy. One advantage provided by these embodiments is that contaminating, non-tumor cells (such as infiltrating lymphocytes or other immune system cells) may be removed as so be absent from affecting the genes identified or the subsequent analysis of gene expression levels as provided herein. Such contamination is present where a biopsy is used to generate gene expression profiles.

In further embodiments of the disclosure utilizing Q-PCR or reverse transcriptase Q-PCR as the assay platform, the expression levels of gene sequences of the disclosure may be compared to expression levels of reference genes in the same sample or a ratio of expression levels may be used. This provides a means to "normalize" the expression data for comparison of data on a plurality of known tumor types and a cell containing sample to be assayed. Moreover, the Q-PCR may be performed in whole or in part with use of a multiplex format.

In an additional aspect, the methods provided by the present disclosure may also be automated in whole or in part. This includes the embodiment of the disclosure in software. Non-limiting examples include processor executable instructions on one or more computer readable storage devices wherein said instructions direct the classification of tumor samples based upon gene expression levels as described herein. Additional processor executable instructions on one or more computer readable storage devices are contemplated wherein said instructions cause representation and/or manipulation, via a computer output device, of the process or results of a classification method.

The disclosure includes software and hardware embodiments wherein the gene expression data of a set of gene sequences in a plurality of known tumor types is embodied as a data set. In some embodiments, the gene expression data set is used for the practice of a method of the disclosure. The disclosure also provides computer related means and systems for performing the methods disclosed herein. In some embodiments, an apparatus for classifying a cell containing sample is provided. Such an apparatus may comprise a query input configured to receive a query storage configured to store a gene expression data set, as described herein, received from a query input; and a module for accessing and using data from the storage in a classification algorithm as described herein. The apparatus may further comprise a string storage for the results of the classification algorithm, optionally with a module for accessing and using data from the string storage in an output algorithm as described herein.

The steps of a method, process, or algorithm described in connection with the embodiments disclosed herein may be embodied directly in hardware, in a software module executed by a processor, or in a combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes.

A further aspect of the disclosure provides for the use of the present disclosure in relation to clinical activities. In some embodiments, the determination or measurement of gene expression as described herein is performed as part of providing medical care to a patient, including the providing of diagnostic services in support of providing medical care. Thus the disclosure includes a method in the medical care of a patient, the method comprising determining or measuring expression levels of gene sequences in a cell containing sample obtained from a patient as described herein. The method may further comprise the classifying of the sample, based on the determination/measurement, as including a tumor cell of a tumor type or tissue origin in a manner as described herein. The determination and/or classification may be for use in relation to any aspect or embodiment of the disclosure as described herein.

The determination or measurement of expression levels may be preceded by a variety of related actions. In some embodiments, the measurement is preceded by a determination or diagnosis of a human subject as in need of said measurement. The measurement may be preceded by a determination of a need for the measurement, such as that by a medical doctor, nurse or other health care provider or professional, or those working under their instruction, or personnel of a health insurance or maintenance organization in approving the performance of the measurement as a basis to request reimbursement or payment for the performance.

The measurement may also be preceded by preparatory acts necessary to the actual measuring. Non-limiting examples include the actual obtaining of a cell containing sample from a human subject; or receipt of a cell containing sample; or sectioning a cell containing sample; or isolating cells from a cell containing sample; or obtaining RNA from cells of a cell containing sample; or reverse transcribing RNA from cells of a cell containing sample. The sample may be any as described herein for the practice of the disclosure.

The disclosure further provides kits for the determination or measurement of gene expression levels in a cell containing sample as described herein. A kit will typically comprise one or more reagents to detect gene expression as described herein for the practice of the present disclosure. Non-limiting examples include polynucleotide probes or primers for the detection of expression levels, one or more enzymes used in the methods of the disclosure, and one or more tubes for use in the practice of the disclosure. In some embodiments, the kit will include an array, or solid media capable of being assembled into an array, for the detection of gene expression as described herein. In other embodiments, the kit may comprise one or more antibodies that is immunoreactive with epitopes present on a polypeptide which indicates expression of a gene sequence. In some embodiments, the antibody will be an antibody fragment.

A kit of the disclosure may also include instructional materials disclosing or describing the use of the kit or a primer or probe of the present disclosure in a method of the disclosure as provided herein. A kit may also include additional components to facilitate the particular application for which the kit is designed. Thus, for example, a kit may additionally contain means of detecting the label (e.g. enzyme substrates for enzymatic labels, filter sets to detect fluorescent labels, appropriate secondary labels such as a sheep anti-mouse-HRP, or the like). A kit may additionally include buffers and other reagents recognized for use in a method of the disclosure.

Having now generally provided the disclosure, the same will be more readily understood through reference to the following examples which are provided by way of illustration, and are not intended to be limiting of the disclosure, unless specified.

EXAMPLES

Example 1

Expression Levels of PANX3 (Pannexin3)

Figure 1:
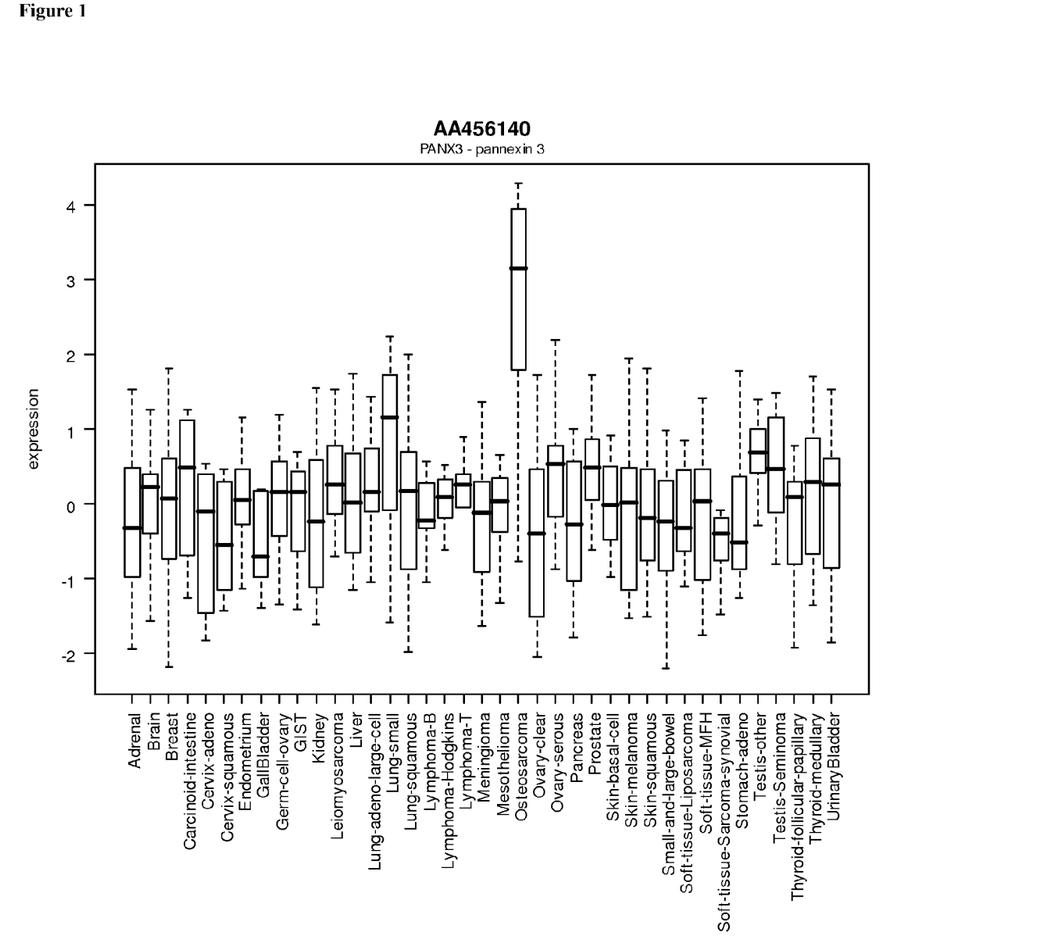
FIG. 1 illustrates the range of expression levels of a first transcribed sequence of the disclosure in 39 of the 54 disclosed tumor types.

The expression level of PANX3 (pannexin 3) in multiple samples of a plurality of 39 known tumor types from human subjects was determined and the results are shown in FIG. 1. The range of the expression level in each tumor type overlapped significantly in 38 of the 39 tumor types.

Example 2

Expression Levels of BATF

Figure 2:
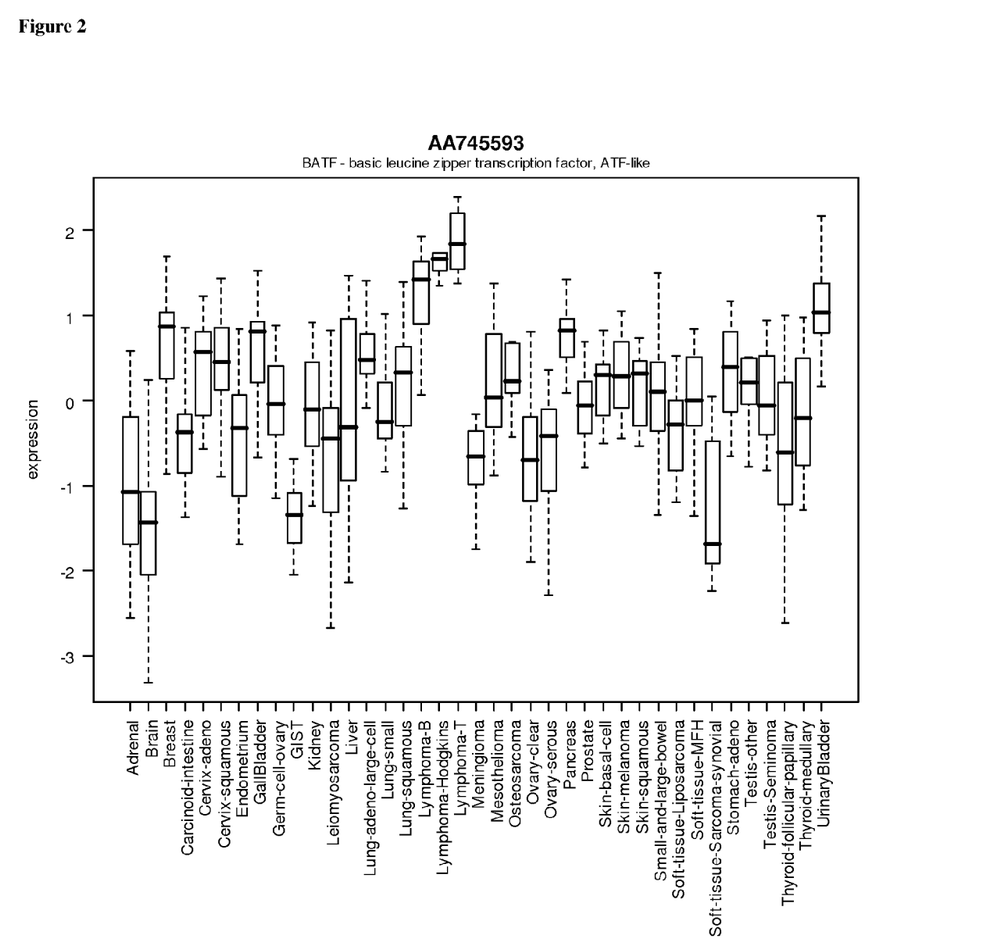
FIG. 2 illustrates the range of expression levels of a second transcribed sequence of the disclosure in 39 of the 54 disclosed tumor types.

The expression level of BATF (basic leucine zipper transcription factor, ATF-like) in multiple samples of the plurality of 39 known tumor types of Example 1 was determined and the results are shown in FIG. 2. The range of the expression level in each tumor type overlapped among members of all 39 tumor types.

Example 3

Expression Levels of Additional Transcribed Sequences

The expression levels of the additional 85 transcribed sequences as disclosed herein were determined in the same manner as Examples 1 and 2 across the same 39 tumor types. The ranges of expression levels for each transcribed sequence were observed to overlap between multiple tumor types.

Example 4

Expression Levels of Transcribed Sequences in Additional Tumor Types

The expression levels of each of the 87 transcribed sequences as disclosed herein were determined in the same manner as Examples 1 and 2 across the disclosed 54 tumor types. The ranges of expression levels for each transcribed sequence were observed to overlap between multiple tumor types.

All references cited herein, including patents, patent applications, and publications, are hereby incorporated by reference in their entireties, whether previously specifically incorporated or not.

Having now fully described the inventive subject matter, it will be appreciated by those skilled in the art that the same can be performed within a wide range of equivalent parameters, concentrations, and conditions without departing from the spirit and scope of the disclosure and without undue experimentation.

While this disclosure has been described in connection with specific embodiments thereof, it will be understood that it is capable of further modifications. This application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth.

What is claimed is:

1. A method of classifying a cell-containing sample as containing tumor cells of a type of tissue, said method comprising
producing cDNA copies of 50 or more transcribed sequences from cells in a cell-containing sample obtained from a human subject, wherein said 50 or more transcribed sequences comprise at least a portion of each of the following genes: Basic leucine zipper transcription factor, ATF-like (BATF); B-cell CLL/lymphoma 11B (BCL11B); Cyclin A1 (CCNA1); Cell division cycle associated 3 (CDCA3); Cadherin 16, KSP-cadherin (CDH16); Cadherin 17, LI cadherin (CDH17); Cadherin, EGF LAG seven-pass G-type receptor 2 (CELSR2); Cholinergic receptor, muscarinic 3 (CHRM3); Colony-stimulating factor 2 receptor, beta, low-affinity (granulocyte-macrophage) (CSF2RB); Chemokine (C-X3-C motif) receptor 1 (CX3CR1); Chromosome Y open reading frame 15A (CYorf15A); Empty spiracles homolog 2 (EMX2); Estrogen receptor 1 (ESR1); Hypothetical LOC388416, non-coding RNA; CDNA FLJ44317 fis, clone TRACH3000586; Hypothetical LOC400951; Fibroblast growth factor 9 (FGF9); Forkhead box A1 (FOXA1); Forkhead box G1A (FOXG1B); Gap junction protein, beta 6 (connexin 30) (GJB6); Hepatic leukemia factor (HLF); Homeobox A9 (HOXA9); Homeobox B8 (HOXB8); Homeobox C10 (HOXC10); Homeobox D11 (HOXD11); 5-hydroxytryptamine (serotonin) receptor 3A (HTR3A); Iroquois Homeobox 3 (IRX3); RAX-like homeobox (ISX); Potassium inwardly rectifying channel, subfamily J, member 11 (KCNJ11); Kinesin family member 12 (KIF12); Kinesin family member 2C (KIF2C); Mitogen-activated protein kinase kinase 6 (MAP2K6); Myeloid ecotropic viral integration site 1 homoloq (MEIS1); Paired box gene 8 (PAX8); Prostate cancer-associated protein 6 (PCANAP6); Peroxisome proliferative activated receptor, gamma (PPARG); Preferentially expressed antigen in melanoma (PRAME); Regulator of G-protein signalling 17 (RGS17); S100 calcium binding protein P (S100P); SH2 domain protein 1A (SH2D1A); Hypothetical LOC389142 (SLC25A23); Solute carrier family 35, member F3 (SLC35F3); Solute carrier family 43, member 1 (SLC43A1); Solute carrier family 6, member 13 (SLC6A13); Solute carrier family 7, member 5 (SLC7A5); Hypothetical protein LOC253970 (TITF1); Transmembrane protease, serine 3 (TMPRSS3); Transmembrane protease serine 4 (TMPRSS4); Thyroid-stimulating hormone receptor (TSHR), and Uroplakin 1B (UPK1B), amplifying said cDNA copies to produce amplified molecules, comparing said expression levels of 50 or more transcribed sequences to expression levels of the same 50 or more transcribed sequences in a plurality of known tumor types comprising one or more known tumor tissues selected from adrenal-cortical tumor, tumor of the salivary gland, squamous cell carcinoma, neuroendocrine-pancreas cancer, merkel cell carcinoma, lung carcinoid, primitive neuroectodermal tumor, sex cord stromal tumor, thymic carcinoma/thymoma, adenocarcinoma of urinary bladder, and squamous cell carcinoma of urinary bladder; and classifying the sample as containing or not containing tumor cells of a tumor type or tissue in said plurality.

2. The method of claim 1 wherein the plurality comprises adrenal-cortical tumor, tumor of the salivary gland, squamous cell carcinoma, neuroendocrine-pancreas cancer, merkel cell carcinoma, lung carcinoid, primitive neuroectodermal tumor, sex cord stromal tumor, thymic carcinoma/thymoma, adenocarcinoma of urinary bladder, and squamous cell carcinoma of urinary bladder, and said classifying is of the sample as containing or not containing tumor cells of an adrenal-cortical tumor, tumor of the salivary gland, squamous cell carcinoma, neuroendocrine-pancreas cancer, merkel cell carcinoma, lung carcinoid, primitive neuroectodermal tumor, sex cord stromal tumor, thymic carcinoma/thymoma, adenocarcinoma of urinary bladder, and squamous cell carcinoma of urinary bladder.

3. The method of claim 2 wherein the plurality comprises adrenal-cortical tumor, adrenal pheochromocytoma, tumor of the brain, adenocarcinoma of breast, cervical adenocarcinoma, cervical squamous cell carcinoma, cholangiocarcinoma, endometrial adenocarcinoma, esophageal squamous cell carcinoma, gastrointestinal stromal tumor, adenocarcinoma of gallbladder, gastro-esophageal adenocarcinoma, seminomatous germ cell tumor, nonseminomatous germ cell tumor, tumor of the salivary gland, squamous cell carcinoma, colorectal adenocarcinoma, small intestine adenocarcinoma, clear cell renal cell carcinoma, chromophobe renal cell carcinoma, papillary renal cell carcinoma, hepatocellular carcinoma, lung adenocarcinoma, lung squamous cell carcinoma, lymphoma, melanoma, meningioma, mesothelioma, small/large cell neuroendocrine lung cancer, neuroendocrine-pancreas cancer, merkel cell carcinoma, gastrointestinal carcinoid, lung carcinoid, clear cell adenocarinoma, endometrioid adenocarcinoma, mucinous adenocarcinoma, serous adenocarcinoma, pancreatic adenocarcinoma, prostate adenocarcinoma, malignant fibrous histiocytoma, primitive neuroectodermal tumor, leiomyosarcoma, liposarcoma, osteosarcoma, synovial sarcoma, sex cord stromal tumor, basal cell carcinoma, skin squamous cell carcinoma, thymic carcinoma/thymoma, follicular/papillary carcinoma, medullary carcinoma, transitional cell carcinoma, adenocarcinoma of bladder, and squamous cell carcinoma of bladder, and said classifying is of the sample as containing or not containing tumor cells of an adrenal-cortical tumor, adrenal pheochromocytoma, tumor of the brain, adenocarcinoma of breast, cervical adenocarcinoma, cervical squamous cell carcinoma, cholangiocarcinoma, endometrial adenocarcinoma, esophageal squamous cell carcinoma, gastrointestinal stromal tumor, adenocarcinoma of gallbladder, gastro-esophageal adenocarcinoma, seminomatous germ cell tumor, nonseminomatous germ cell tumor, tumor of the salivary gland, squamous cell carcinoma, colorectal adenocarcinoma, small intestine adenocarcinoma, clear cell renal cell carcinoma, chromophobe renal cell carcinoma, papillary renal cell carcinoma, hepatocellular carcinoma, lung adenocarcinoma, lung squamous cell carcinoma, lymphoma, melanoma, meningioma, mesothelioma, small/large cell neuroendocrine lung cancer, neuroendocrine-pancreas cancer, merkel cell carcinoma, gastrointestinal carcinoid, lung carcinoid, clear cell adenocarinoma, endometrioid adenocarcinoma, mucinous adenocarcinoma, serous adenocarcinoma, pancreatic adenocarcinoma, prostate adenocarcinoma, malignant fibrous histiocytoma, primitive neuroectodermal tumor, leiomyosarcoma, liposarcoma, osteosarcoma, synovial sarcoma, sex cord stromal tumor, basal cell carcinoma, skin squamous cell carcinoma, thymic carcinoma/thymoma, follicular/papillary carcinoma, medullary carcinoma, transitional cell carcinoma, adenocarcinoma of bladder, and squamous cell carcinoma of bladder.

4. The method of claim 1 wherein all said expression levels are determined by use of a microarray.

5. The method of claim 1 wherein said classifying is with an accuracy of 60% or higher.

6. The method of claim 1 wherein said amplification comprises linear RNA amplification or quantitative PCR.

7. The method of claim 6 wherein said amplification is quantitative PCR amplification of at least 50 nucleotides of the transcribed sequences.

8. The method of claim 1, wherein cDNA copies of 50 to 100 transcribed sequences are produced.

9. The method of claim 1, wherein said sample is a formalin fixed, paraffin embedded (FFPE) sample.

10. The method of claim 1, wherein a majority of the expression levels of 50 or more transcribed sequences overlap in said plurality.

11. The method of claim 1, wherein 30 or more of the expression levels of 50 or more transcribed sequences overlap in said plurality.

12. The method of claim 1, wherein 35 or more of the expression levels of 50 or more transcribed sequences overlap in said plurality.

13. The method of claim 1, wherein 40 or more of the expression levels of 50 or more transcribed sequences overlap in said plurality.

14. The method of claim 8, wherein 55 or more of the expression levels of 50 or more transcribed sequences overlap in said plurality.

15. The method of claim 8, wherein 60 or more of the expression levels of 60 or more transcribed sequences overlap in said plurality.

* * * * *